(12) United States Patent
Morrison et al.

(10) Patent No.: US 11,357,560 B2
(45) Date of Patent: Jun. 14, 2022

(54) DUAL-FUNCTION ANCHOR SYSTEM

(71) Applicant: Trace Orthopedics LLC, Philadelphia, PA (US)

(72) Inventors: William B. Morrison, Delran, NJ (US); Adam J. Greenspan, Philadelphia, PA (US)

(73) Assignee: Trace Orthopedics, LLC, Philadelphia, PA (US)

( * ) Notice: Subject to any disclaimer, the term of this patent is extended or adjusted under 35 U.S.C. 154(b) by 0 days.

(21) Appl. No.: 16/629,428

(22) PCT Filed: Jul. 9, 2018

(86) PCT No.: PCT/US2018/041346
§ 371 (c)(1),
(2) Date: Jan. 8, 2020

(87) PCT Pub. No.: WO2019/014155
PCT Pub. Date: Jan. 17, 2019

(65) Prior Publication Data
US 2020/0138497 A1 May 7, 2020

Related U.S. Application Data

(60) Provisional application No. 62/530,502, filed on Jul. 10, 2017, provisional application No. 62/693,154, filed on Jul. 2, 2018.

(51) Int. Cl.
*A61B 17/04* (2006.01)
*A61B 17/86* (2006.01)
(Continued)

(52) U.S. Cl.
CPC ........ *A61B 17/869* (2013.01); *A61B 17/3423* (2013.01); *A61B 17/8615* (2013.01);
(Continued)

(58) Field of Classification Search
CPC combination set(s) only.
See application file for complete search history.

(56) References Cited

U.S. PATENT DOCUMENTS 5,006,023 A 4/1991 Kaplan
6,276,883 B1 8/2001 Unsworth et al.
(Continued)

FOREIGN PATENT DOCUMENTS

CN 204413957 U 6/2015

OTHER PUBLICATIONS

International Search Report and Written Opinion, International Patent Application No. PCT/US2018/041346, dated Sep. 28, 2018.
(Continued)

*Primary Examiner* — Sameh R Boles
(74) *Attorney, Agent, or Firm* — Saul Ewing Arnstein & Lehr LLP; Brian R. Landry

(57) ABSTRACT

A surgical tool, comprising a needle comprising an aperture of sufficient diameter for receiving a screw; a tool, insertable into said aperture for inserting said screw and capable of engaging with and turning the screw; said screw comprising a shaft having threads in a first direction, a head having a bottom face having a flange, and a coil; said coil wound around the screw shaft in an opposing second direction as to the first direction; said coil comprising a coil end which is defined to engage with the flange on the bottom face.

19 Claims, 10 Drawing Sheets

(51) Int. Cl.
    *A61F 2/08*     (2006.01)
    *A61B 17/34*    (2006.01)
    *A61B 17/88*    (2006.01)
    *A61B 17/00*    (2006.01)
(52) U.S. Cl.
    CPC ...... *A61B 17/8625* (2013.01); *A61B 17/8888* (2013.01); *A61F 2/0811* (2013.01); *A61B 2017/00004* (2013.01); *A61B 2017/0088* (2013.01); *A61B 2017/8655* (2013.01); *A61F 2002/0858* (2013.01)

(56) References Cited

U.S. PATENT DOCUMENTS

| | | |
|---|---|---|
| 6,514,257 B2 | 2/2003 | Dovesi et al. |
| 6,656,184 B1 | 12/2003 | White et al. |
| 8,043,333 B2 | 10/2011 | Frigg et al. |
| 9,427,270 B2 | 8/2016 | Housman |
| 9,675,353 B2 | 6/2017 | Ranucci et al. |
| 2002/0077631 A1* | 6/2002 | Lubbers ............... A61F 2/0811 606/232 |
| 2010/0256690 A1 | 10/2010 | Appenzeller et al. |
| 2013/0338706 A1 | 12/2013 | Jimenez et al. |

OTHER PUBLICATIONS

Communication pursuant to Rule 164(1) EPC, Partial Supplementary European Search Report, European Patent Application No. 18832814.0, dated Mar. 22, 2021, 11 pages.

Communication, European Patent Application No. 18832814.0, dated Jun. 23, 2021, 10 pages.

First Office Action, Chinese Patent Application No. 2018800563402, dated Nov. 26, 2021.

Examination Report, Indian Patent Application No. 202017002791, dated Mar. 25, 2022, 7 pages.

* cited by examiner

DUAL-FUNCTION ANCHOR SYSTEM

CROSS-REFERENCE TO RELATED APPLICATIONS

This application is a national phase application under 35 U.S.C. 371 of International Application No. PCT/US2018/041346, filed Jul. 9, 2018, which claims the benefit of U.S. Provisional Application No. 62/530,502 filed Jul. 10, 2017, and U.S. Provisional Application No. 62/693,154 filed Jul. 2, 2018. The entire contents of each application is hereby incorporated by reference herein.

FIELD OF INVENTION

The present invention is generally related to medical implant devices, particularly towards certain surgical implant tools for attaching torn tissue to a bone surface.

BACKGROUND OF INVENTION

Movement of the human body requires complex communication between the structural components, namely the muscles, tendons, bones, and vasculature, and the electrical pulses that control the muscles to create movement. Over time, the body ages, namely the muscles, tendons, and bones wear and damage can occur. For example, a frequent issue is that the muscle or tendon tears away from the bone. Both partial tears and complete tears may result in retraction that must be surgically repaired.

Certain soft tissues (muscle or tendon) insert parallel to the bone via a fascial plane. For example, pubalgia is seen with a variety of athletic activities, and is an injury frequently seen in active and young men and women. This happens when the rectus abdominis and adductor aponeurosis are disengaged from the pubic bone. At the same time, another population of patients, senior patients, have tears of the gluteus tendon. Both injuries are typically repaired with open surgery, as it is otherwise difficult to properly secure the tissue and ensure recovery.

Indeed, both injuries also have significant issues for the patient population. For recreational and professional athletes, the injury recovery is 4-12 months, and limits ability for those to enjoy activities or to participate in their profession. For senior populations, these gluteus injuries and related hip fractures occur with significant regularity and are a significant risk for morbidity and mortality due to the damage from the injury.

To optimally heal this type of injury in a minimally invasive fashion, a specialized system is needed which includes components used in vivo and ex vivo. Biocompatibility and mechanical performance are critical aspects of the implantable components in such a system, and a given implantation site carries distinct considerations relating to both biocompatibility and mechanical performance.

For anchoring within bone tissue, rigid-high strength material is needed to effectively position the device into bone tissue. This includes generating sufficient torque to penetrate the bone tissue as well as possessing sufficient strength to establish and maintain fixation for the desired time period, in this case at least 6 months. For gripping and positioning soft tissues, a ductile material is needed to effectively position the device into soft tissue. This includes deforming temporarily under force exerted associated with positioning while maintaining appropriate strength. The ability to accomplish these functions is determined by the component composition. Parameters such as elastic modulus, tensile strength, shear strength, flexural strength shall guide the selection of suitable materials for the respective components.

SUMMARY OF INVENTION

The device of the embodiments described herein, and the method(s) of use and of treatment is designed to re-attach torn tissue to bone through a needle—avoiding the need for open surgery. Other suitable uses may also exist where soft tissue can be secured with a coil portion and then the soft tissue can be secured to aid in healing of the tissue.

In a preferred embodiment, a device comprises an applicator and an implantable screw; the implantable screw comprising a shaft comprising threads in a first direction, and a head, having a top and a bottom; the threads extending from an end of the shaft to the bottom of the head; positioned on the bottom of the head is a flange; engaged to the screw is a washer with an offset limb capable of engaging to the flange, and a coil having a first and second end, wound counter-clockwise on the shaft, the first end being engaged to the offset limb of the washer and the second end with an open end.

The device functions by rotating the screw in a counter-clockwise manner to deploy the coil into soft tissue, and then turning the screw in a clockwise manner to advance the screw into the bone. By turning in the clockwise manner, the coil disengages from the shaft and holds the tissue. In certain embodiments, the thread directions can be reversed, without modifying the function of the various embodiments herein.

Accordingly, a preferred embodiment is directed towards a method of securing tissue comprising: placing a screw onto a tissue surface; said screw comprising an implantable screw; the implantable screw comprising a shaft comprising threads in a first direction, and a head, having a top and a bottom; the threads extending from an end of the shaft to the bottom of the head; positioned on the bottom of the head is a flange; engaged to the screw is a washer with an offset limb capable of engaging to the flange, and a coil having a first and second end, wound counter-clockwise on the shaft, the first end being engaged to the offset limb of the washer and the second end with a sharp end; rotating said screw in a counter-clockwise manner to deploy the coil into soft tissue, and then rotating the screw in a clockwise manner to advance the screw into the bone and disengaging the coil by turning the screw in the clockwise manner, wherein the coil also advanced by the larger circumference screw head, attaches the soft tissue caught by the coil onto the bone and held in place by the screw. In preferred embodiments the sharp end has an open end with an outward curve away from the screw, and in certain embodiments, the tip is beveled, with the bevel face open at inner aspect.

In preferred embodiments, the screw and coil can be made of bioabsorbable materials, coated with vascular or bone stimulating materials, be of a bio-compatible metallic or non-metallic material for non-absorbable function, or a combination of these options as necessary for the particular application.

A further embodiment is directed towards a device comprising an expandable coil with counterclockwise winding attached to an anchor screw with standard clockwise threads. This construct is attached to a stylet that is within an outer sheath. The system is passed percutaneously (using imaging guidance) to the bone target. The sheath is retracted, exposing the coil. A counterclockwise turn of the stylet causes the coil to open and expand beyond the margins of the sheath, clasping the surrounding tissue that had become detached from bone. The stylet is then advanced and turned clockwise, causing the anchor to enter the bone. During clockwise turning the coil disengages from the screw shaft and remains expanded, but it is held in place against the bone surface by the screw head.

In certain preferred embodiments, the implanted components would be composed of a bioabsorbable material. This would secondarily result in local inflammation, stimulating neovascularization and healing response. In preferred embodiments, the material may be further coated with a healing therapeutic or the therapeutic can be delivered from the needle at the wound site.

In a preferred embodiment, a device comprises an applicator and an implantable screw; the implantable screw comprising a shaft comprising threads in a first direction, and a head, having a top and a bottom; the threads extend from an end of the shaft to the bottom of the head; positioned on the bottom of the head is a flange; the flange with a tunnel, engaging a coil, said coil having a first and second end, and wound counter-clockwise on the shaft, the first end being engaged to the flange tunnel and the second end with an open end.

Preferably, the device functions by rotating the screw in a counter-clockwise manner to deploy the coil into soft tissue, and then turning the screw in a clockwise manner to advance the screw into the bone. By turning in the clockwise manner, the coil disengages from the shaft and holds the tissue.

Accordingly, a method of securing tissue comprises: placing a screw onto a tissue surface; said screw comprising an implantable screw; the implantable screw comprising a shaft comprising threads in a first direction, and a head, having a top and a bottom; the threads extending from an end of the shaft to the bottom of the head; positioned on the bottom of the head is a flange with a tunneled configuration, and a coil having a first and second end, wound counter-clockwise on the shaft, the first end being engaged to the flange tunnel and the second end with a sharp end with an outward curve away from the screw; rotating said screw in a counter-clockwise manner to deploy the coil into soft tissue, and then turning the screw in a clockwise manner to advance the screw into the bone; disengaging the coil from the flange tunnel on the screw by turning in the clockwise manner, wherein the coil also advanced by the larger circumference screw head attaches the soft tissue caught by the coil onto the bone and held in place by the screw. In certain embodiments, the sharp end is an open end having an outward facing tip and a beveled face.

A preferred embodiment is directed towards a surgical screw comprising a shaft having threads in a first direction, a washer, having offset limbs, a head having a bottom face having a flange, and a coil; said coil wound around the screw shaft in an opposing second direction as to the first direction; said coil comprising a coil end which is defined to engage with an offset limb of said washer; a second offset limb of said washer engages to the flange on the bottom face; engaging the end of the shaft and the coil to a soft tissue.

In a further embodiment, a surgical screw comprising a shaft having threads in a first direction, a head having a bottom face having at least one flange, and a coil; said coil wound around the screw shaft in an opposing second direction as to the first direction; said coil comprising a coil end which is defined to engage said at least one flange; engaging the end of the shaft and the coil to a soft tissue. In a preferred embodiment, the surgical screw comprising at least two flanges, said flanges being positioned on opposing sides of the bottom face of the screw head; said coil end engaging to at least one flange, wherein rotation of the screw forges the coil to rotate.

A further preferred embodiment is directed towards a surgical tool, comprising a needle comprising an aperture of sufficient diameter for receiving a screw; a tool, insertable into said aperture for inserting said screw and capable of engaging with and turning the screw; said screw comprising a shaft having threads in a first direction, a washer, having offset limbs, a head having a bottom face having a flange, and a coil; said coil wound around the screw shaft in an opposing second direction as to the first direction; said coil comprising a coil end which is defined to engage with an offset limb of said washer; a second offset limb of said washer engages to the flange on the bottom face.

In certain embodiments, the screw, washer, or coil of any of the embodiments, made of a bio-compatible materials. In certain embodiments, the screw, washer, or coil, are coated with a bone or vascular stimulator, or wherein said components are bio-absorbable.

In certain embodiments, the screw comprising one or more of the following materials: poly(L-lactic acid), poly (D-L-lactic acid), poly(lactic-co-glycolic acid), poly(para-dioxanone), poly(propylene fumarate), copolymers of poly (L-lactic acid and poly(lactic-co-glycolic acid), magnesium based alloys including Mg—Zn, Mg-6Zn, Mg—Zn—Ca, and MgYREZr, and iron-based alloys including Fe—Mn. In certain embodiments, the screw comprising a polymer coating on metal. In certain embodiments, the screw comprising a ceramic material including calcium phosphate, tricalcium phosphate, and hydroxyapatite in a particulate-reinforced polymer matrix. The screw comprising a ceramic material including calcium phosphate, tricalcium phosphate, and hydroxyapatite as a coating.

In certain embodiments, the washer comprising one or more of the following materials: amorphous poly(lactic acid), poly(L-lactic acid), poly(D-L-lactic acid), poly(glycolic acid), poly(lactic-co-glycolic acid), poly(para-dioxanone), poly(propylene fumarate), copolymers of poly(L-lactic acid and poly(lactic-co-glycolic acid), magnesium based alloys including Mg—Zn, Mg-6Zn, Mg—Zn—Ca, and MgYREZr, and iron-based alloys including Fe—Mn. In certain embodiments, the washer comprising a polymer disposed of on a metal. In certain embodiments, the washer comprising a ceramic material including calcium phosphate, tricalcium phosphate, and hydroxyapatite in a particulate-reinforced polymer matrix. In certain embodiments, the washer comprising a ceramic material including calcium phosphate, tricalcium phosphate, and hydroxyapatite as a coating.

In certain embodiments, the coil comprising one or more of the following materials: amorphous poly(lactic acid), poly(L-lactic acid), poly(D-L-lactic acid), poly(lactic-co-glycolic acid), poly(ethylene glycol), poly(caprolactone), copolymers of poly(L-lactic acid and poly(lactic-co-glycolic acid), copolymers of poly(ethylene glycol) and poly(caprolactone), chitosan crosslinked with or without genipin, magnesium based alloys including Mg—Zn, Mg-6Zn, Mg—Zn—Ca, and MgYREZr, and iron-based alloys including Fe—Mn. In certain embodiments, the coil comprising a polymer coating on a metal. In certain embodiments, the coil comprising a ceramic material including calcium phosphate, tricalcium phosphate, and hydroxyapatite in a particulate-reinforced polymer matrix. In certain embodiments, the coil comprising a ceramic material including calcium phosphate, tricalcium phosphate, and hydroxyapatite as a coating.

In certain embodiments, the coil, screw, or washer is non-absorbable.

In a preferred embodiment, a method of repairing a soft tissue when disassociated from a bone comprising: inserting a surgical tool into a tissue, said tool comprising an aperture for inserting a screw and a tool to turn the screw; said screw comprising a shaft having threads in a first direction, a washer, having offset limbs, a head having a bottom face having a flange, and a coil; said coil wound around the screw shaft in an opposing second direction as to the first direction; said coil comprising a coil end which is defined to engage with an offset limb of said washer; a second offset limb of said washer engages to the flange on the bottom face; engaging the end of the shaft and the coil to a soft tissue; rotating the screw in the second direction until said coil is deployed into said tissue a pre-determined amount; rotating said screw in a first direction, until said screw is sufficiently embedded into a bone surface to compress said soft tissue to said bone.

In a preferred embodiment, the method wherein said aperture may further be utilized to inject certain bone or vascular healing compositions to the surgical site.

A further preferred embodiment is directed towards a surgical screw comprising a shaft having threads in a first direction, a head having a bottom face having a flange, the flange having a tunnel, and a coil; said coil wound around the screw shaft in an opposing second direction as to the first direction; said coil comprising a coil end which is defined to engage with the flange tunnel on the bottom face. In a preferred embodiment, the tunnel receives the coil, and the tunnel has a depth from 0 mm to 20 mm, preferably from 1 mm to 10 mm.

A further preferred embodiment comprising a surgical tool, said surgical tool comprising a needle comprising an aperture of sufficient diameter for receiving a screw; a tool, insertable into said aperture for inserting said screw and capable of engaging with and turning the screw; said screw comprising a shaft having threads in a first direction, a head having a bottom face having a flange, the flange having a tunnel, and a coil; said coil wound around the screw shaft in an opposing second direction as to the first direction; said coil comprising a coil end which is defined to engage to the flange tunnel on the bottom face and a curved tip for engaging a tissue.

In certain embodiments, the screw, washer, or coil of any of the embodiments, made of a bio-compatible materials. In certain embodiments, the screw, washer, or coil, are coated with a bone or vascular stimulator, or wherein said components are bio-absorbable.

A further embodiment is directed towards a method of repairing a soft tissue when disassociated from a bone comprising; inserting a surgical tool into a tissue, said surgical tool comprising an aperture for inserting a screw and a tool to turn the screw; said screw comprising a shaft having threads in a first direction, a head having a bottom face having a flange, the flange having a tunnel, and a coil; said coil wound around the screw shaft in an opposing second direction as to the first direction; said coil comprising a coil end which is defined to engage with the flange tunnel on the bottom face; engaging the end of the shaft and the coil to a soft tissue; rotating the screw in the second direction until said coil is deployed into said tissue a pre-determined amount; rotating said screw in a first direction, until said screw is sufficiently embedded into a bone surface to compress said soft tissue to said bone.

A further embodiment is directed towards a surgical screw comprising a shaft having threads in a first direction, a head having a bottom face having a flange, and a coil; said coil wound around the screw shaft in an opposing second direction as to the first direction; said coil comprising a coil end which is defined to engage said flange; engaging the end of the shaft and the coil to a soft tissue. In a preferred embodiment, said flange has a flange tunnel, wherein the coil end engages into the flange tunnel.

A further embodiment is directed towards a surgical tool, comprising a needle comprising an aperture of sufficient diameter for receiving a screw; a tool, insertable into said aperture for inserting said screw and capable of engaging with and turning the screw; said screw comprising a shaft having threads in a first direction, a head having a bottom face having a flange, the flange having a tunnel; and a coil, said coil wound around the screw shaft in an opposing second direction as to the first direction; said coil comprising a coil end which engages to the flange tunnel on the bottom face.

A further preferred embodiment is directed to a method of repairing a soft tissue when disassociated from a bone comprising; inserting a surgical tool, comprising an aperture for inserting a screw and a tool to turn the screw; said screw comprising a shaft having threads in a first direction, a head having a bottom face having a flange, the flange having a tunnel, and a coil; said coil wound around the screw shaft in an opposing second direction as to the first direction; said coil comprising a coil end which is defined to engage with the flange tunnel on the bottom face; engaging the end of the shaft and the coil to a soft tissue; rotating the screw in the second direction until said coil is deployed into said tissue a pre-determined amount; rotating said screw in a first direction, until said screw is sufficiently embedded into a bone surface to compress said soft tissue to said bone. A further embodiment comprises a step of injecting a therapeutic to the wound site selected from a bone healing composition, a vascular healing composition, an antibiotic or combinations thereof. In a further embodiment, the coil or the screw is coated with a therapeutic selected from the group consisting of a bone healing composition, a vascular healing composition, an antibiotic, or combinations thereof.

In certain embodiments, the screw comprising one or more of the following materials: poly(L-lactic acid), poly (D-L-lactic acid), poly(lactic-co-glycolic acid), poly(para-dioxanone), poly(propylene fumarate), copolymers of poly (L-lactic acid and poly(lactic-co-glycolic acid), magnesium based alloys including Mg—Zn, Mg-6Zn, Mg—Zn—Ca, and MgYREZr, and iron-based alloys including Fe—Mn. In certain embodiments, the screw comprising a polymer of coating on a metal. In certain embodiments, the screw comprising a ceramic material including calcium phosphate, tricalcium phosphate, and hydroxyapatite in a particulate-reinforced polymer matrix. The screw comprising a ceramic material including calcium phosphate, tricalcium phosphate, and hydroxyapatite as a coating.

In certain embodiments, the coil comprising one or more of the following materials: amorphous poly(lactic acid), poly(L-lactic acid), poly(D-L-lactic acid), poly(lactic-co-glycolic acid), poly(ethylene glycol), poly(caprolactone), copolymers of poly(L-lactic acid and poly(lactic-co-glycolic acid), copolymers of poly(ethylene glycol) and poly(caprolactone), chitosan crosslinked with or without genipin, magnesium based alloys including Mg—Zn, Mg-6Zn, Mg—Zn—Ca, and MgYREZr, and iron-based alloys including Fe—Mn. In certain embodiments, the coil comprising a polymer coating on a metal. In certain embodiments, the coil comprising a ceramic material including calcium phosphate, tricalcium phosphate, and hydroxyapatite in a particulate-reinforced polymer matrix. In certain embodiments, the coil comprising a ceramic material including calcium phosphate, tricalcium phosphate, and hydroxyapatite as a coating.

In a further embodiment, a surgical screw comprising a shaft having threads in a first direction, a head having a bottom face having at least one flange, and a coil; said coil wound around the screw shaft in an opposing second direction as to the first direction; said coil comprising a coil end which is defined to engage said at least one flange; engaging the end of the shaft and the coil to a soft tissue. In a preferred embodiment, the surgical screw comprising at least two flanges, said flanges being positioned on opposing sides of the bottom face of the screw head; said coil end engaging to at least one flange, wherein rotation of the screw forges the coil to rotate. In a preferred embodiment, the screw comprising an indentation on the bottom face of the screw head, said indentation positioned adjacent to the shaft and extending to a flange. In a further preferred embodiment, the screw comprising at least two flanges, said flanges positioned on the bottom face and positioned on the outer portion of the indentation. In a further preferred embodiment, wherein the coil engages the inner portion of at least one flange, which is the indentation. In a further embodiment, the screw, wherein said coil comprises an outward curved tip having a beveled face open at inner aspect

BRIEF DESCRIPTION OF THE DRAWINGS

FIG. 3A depicts use of a washer, to aid coil movement, FIG. 3B depicts a tunnel flange head to aid coil movement; FIG. 3C depicts a bottom flange; and FIG. 3D depicts a detail of the tip of the coil and the bevel.

DETAILED DESCRIPTION OF THE FIGURES

Soft tissue injuries can be particular debilitating to both young and old alike. Male and female athletes are commonly faced with debilitating adductor and abdominal tears, where the tendon or muscle is disengaged from the bone. To repair these injuries, platelet rich plasma has been utilized, with unproven results. Other options include open surgical procedures, but these face long recovery times.

For older patients, those over age of 65, age related injuries include risk of hip fracture related to gluteus tendon tears. These common injuries result in weakness of the gluteus muscles and leads to sagging of the pelvis, tilting and to Trendelenburg gait. Ultimately, these weaknesses lead to debilitation and increase the risk of falls. Hip fractures occur at nearly 250,000 a year in the United States, and lead to significant impairment and risk of mortality.

The surgical procedures that are available are inadequate as they have significant recovery times and for certain patients increase the risk of secondary infection or other disease progression. Accordingly, new strategies are necessary to repair soft tissues that are disengaged from bone. Herein, embodiments describe an anchor system comprising a screw and a coil suitable for engaging soft tissue and bone.

Figure 1:
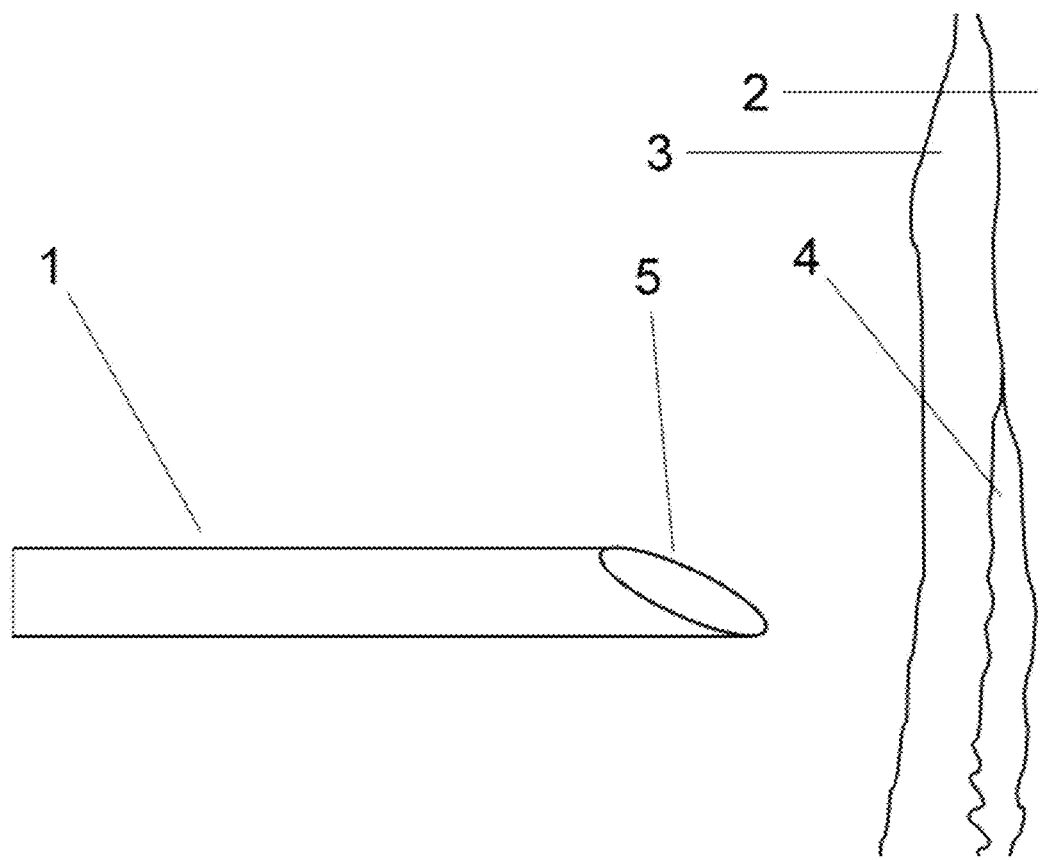
FIG. 1 depicts a needle inserted adjacent to soft tissue, which is separated from the bone.

FIG. 1 depicts a soft tissue 3, generally a muscle or a tendon that is disengaged from the bone 2. The disengagement space 4 is the injury that is being rectified by the surgical tool described herein. In a healthy scenario, the soft tissue 3 is attached to the bone 2. The presence of disengagement space 4 is the injury, where the soft tissue 3 is separated from the bone 2.

FIG. 1 further depicts a needle entering the tissue space. The needle 1 is inserted into the tissue around the injury under normal insertion protocols. This can be completed with imaging guidance, by hand, or by other means as is known to a person of ordinary skill in the art. The needle aperture 5 is defined to allow for deployment of a tool for insertion of the device screw as depicted in further figures.

Figure 2:
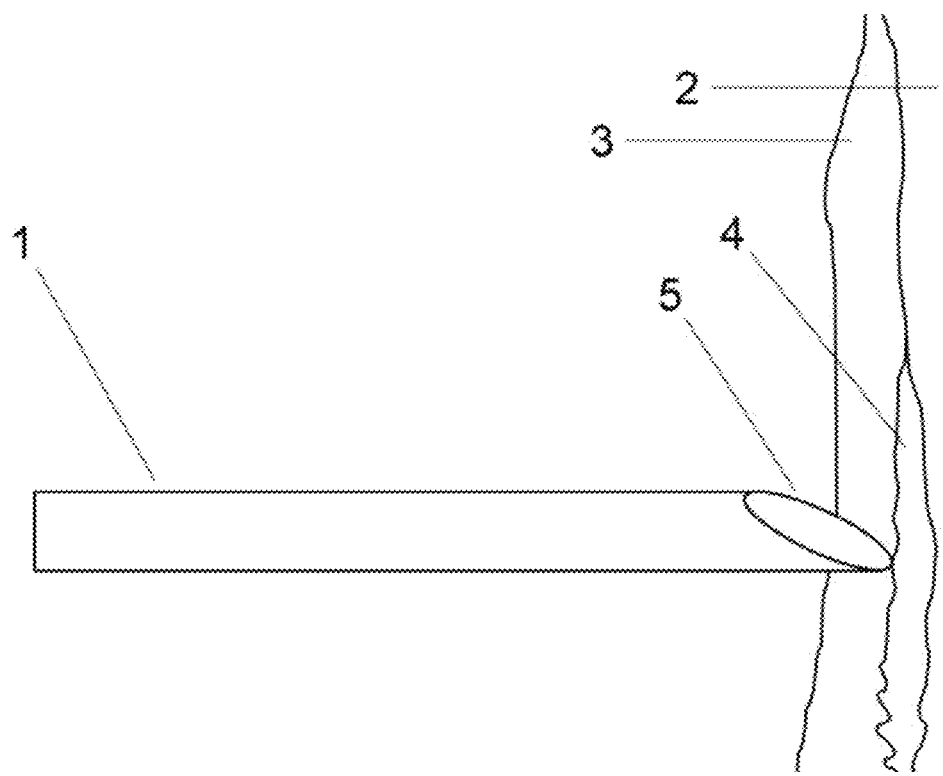
FIG. 2 depicts the needle inserted into soft tissue.

FIG. 2 depicts a further advancement of the needle 1 into the soft tissue 3, with the tip of the needle 1 inserted into the soft tissue 3. For deployment, the needle can also be adjacent to the soft tissue, allowing the tip of the screw or the coil to first penetrate the soft tissue, and allowing for deployment of the coil as described herein.

Figure 3A:
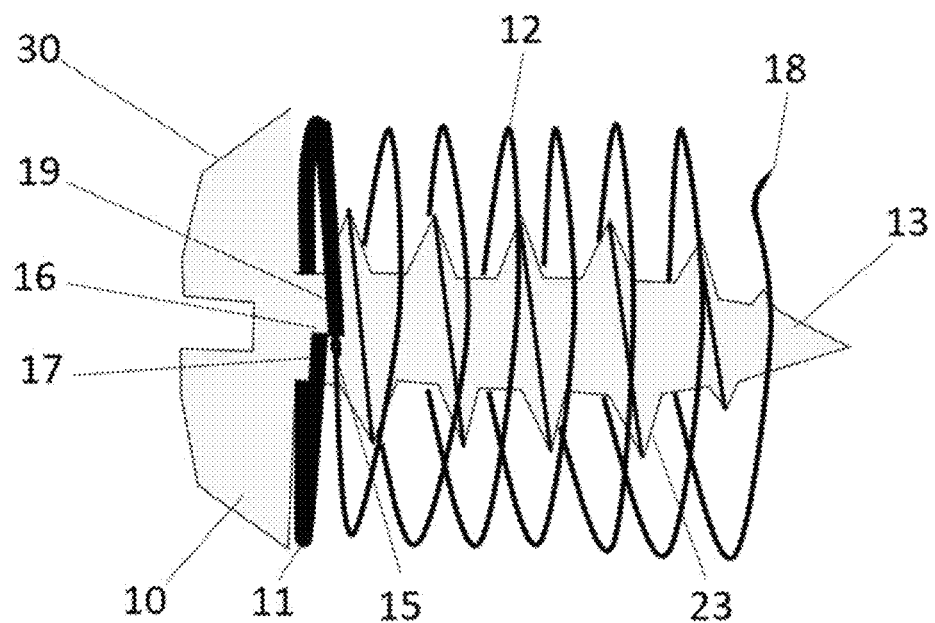
FIGS. 3A, 3B, 3C, and 3D depict detail of an embodiment of a screw with counter-clockwise wound coil.

FIG. 3A depicts an orthopedic screw 30 that is used to attach the soft tissue 3 to the bone 2 of FIGS. 1 and 2. The orthopedic screw 30 comprises a head 10 and a shaft 13 with threads 23. The head 10 comprises a head flange 16 positioned on the bottom of the head. This head flange 16 has a washer 11 having an offset flange 17. This offset flange 17 engages with the coil 12 when the screw is turned counter-clockwise and releases the coil when the screw is turned clockwise and advanced. In certain embodiments, the washer 11 can be eliminated and the coil 12 directly contacting the head flange 16.

The flange 16 uses the offset flange 17 of the washer 11 to engage to the coil end 15. The coil end 15 may comprise a rough cut end of the coil material, a blunt end or a rounded or tightly wound section of the coil material, to aid in contacting the offset flange 17. The coil tip 18 is sharpened and curved outward relative to the coil winding. FIG. 3D details an embodiment of the coil tip, with an outward curved tip having a beveled face 41 open at inner aspect. The coil 12 is wound onto the screw shaft 13 in a counter-clockwise manner. By contrast, the threads on the shaft 13 are wound in a clockwise manner. Those of skill in the art will recognize that the standard threads are right-handed threads, wherein driving the screw in a clockwise manner drives the screw into a material. Accordingly, the screw and the coil will have opposing orientation to allow driving of the coil into soft tissue by rotation in one direction and driving of the screw into the bone by opposing rotation. The handed-ness of the screw or coil can be exchanged, as long as there are opposing orientations. The design allows for the first soft tissue rotation without impacting the subsequent opposing rotation to drive the screw, without withdrawing the coil from the soft tissue.

The coil 12, and the screw 30 may be manufactured out of a bio-absorbable material, so that after a pre-determined amount of time, each component can be absorbed into the body. However, it may also be suitable to have each component be manufactured of a non-bio absorbable material, but simply a biocompatible material, for permanent positioning in the body. Alternatively, it may be advisable to have certain components be bio-absorbable and others non-absorbable, for example, the coil may bio-absorb, but the screw may be non-absorbable. Any combination of absorbable or non-absorbable can be utilized as necessary.

Figure 3B:
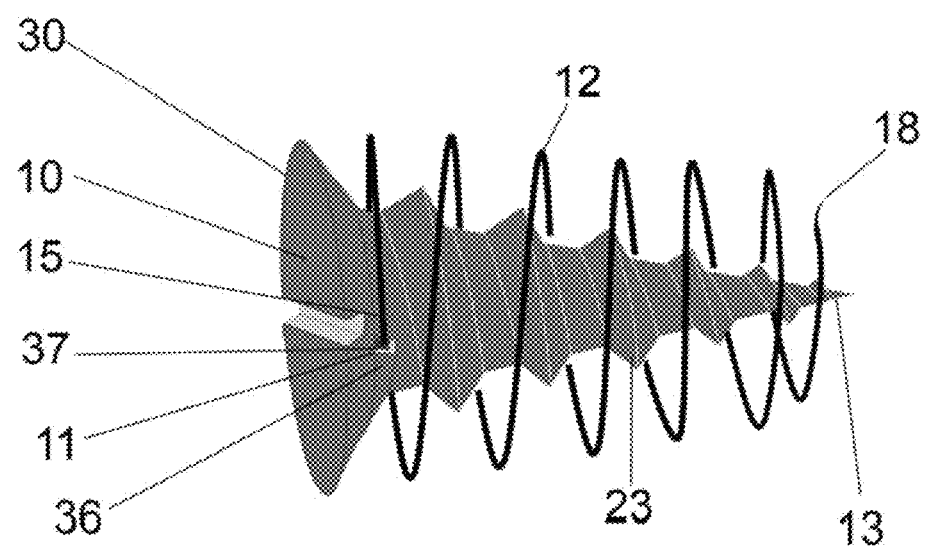

FIG. 3B depicts a further embodiment of an orthopedic screw 30 that is used to attach the soft tissue 3 to the bone 2. The orthopedic screw 30, like FIG. 3A, comprises a head 10, a shaft 13 with threads 23. The head 10 comprises a head flange 16 positioned on the bottom of the head. However, this embodiment comprises a head tunnel flange 36 has an end 11, containing a tunnel 37. This tunnel 37 engages and holds the coil 12 when the screw is turned counter-clockwise, releasing the coil when the screw is turned clockwise and advanced. The tunnel 37 may be a slight indentation, allowing a portion of the coil to enter and be held within the tunnel, for example at a depth of 0-20 mm, preferably 1-10 mm. Alternatively, the tunnel 37 may be merely a protrusion flange (e.g. 0 mm depth), or a simply an indent to catch the coil end.

The tunnel flange 36 uses the tunnel 37 to engage to the coil end 15, wherein certain embodiments the coil end 15 is within the tunnel 37. The coil tip 18 is sharpened and curved outward relative to the coil winding. The coil 12 is wound onto the screw shaft 13 in a counter-clockwise manner. By contrast, the threads on the shaft 13 are wound in a clockwise manner. Those of skill in the art will recognize that the standard threads are right-handed threads, wherein driving the screw in a clockwise manner drives the screw into a material. Accordingly, the screw and the coil will have opposing orientation to allow driving of the coil into soft tissue by rotation in one direction and driving of the screw into the bone by opposing rotation. The design allows for the first soft tissue rotation without impacting the subsequent opposing rotation to drive the screw, without withdrawing the coil (coil) from the soft tissue.

Figure 3C:
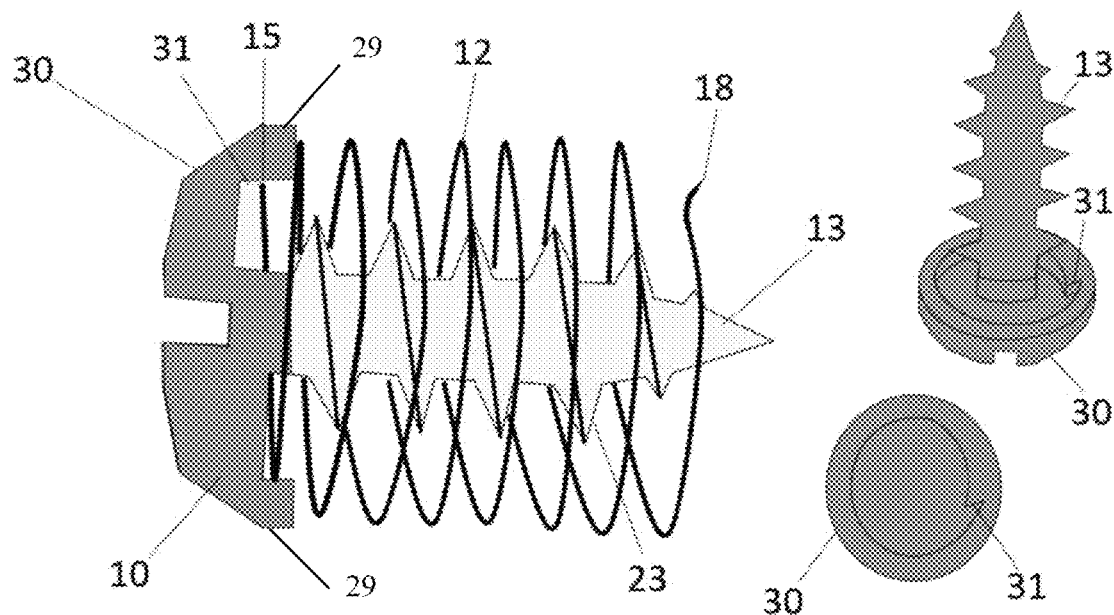
Figure 3D:
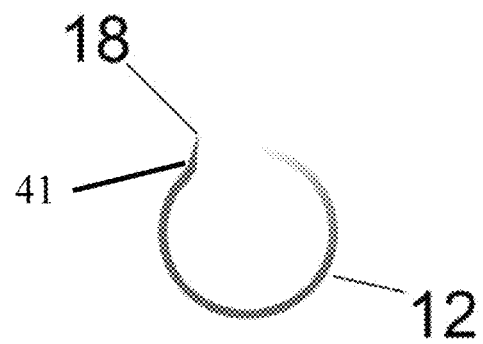

FIG. 3C provides a further embodiment, wherein the bottom of the screw head includes and first and second flange 29, or optionally just a single flange. The one or more flanges function in a similar manner to the tunnel flange 36 and the tunnel 37, or to the washer of FIG. 3A having flanges. As depicted in FIG. 3C, an indentation 31 adjacent to the stem of the screw is provided with the flange 29 near the outer edge of the underside of the screw face. The inner portion of the indentation is adjacent to the stem, while the outer portion of the indentation forms the inner face of the flange 29. This allows the coil end to sit within the indentation. These flanges force the end of the coil to rotate, thus forcing the tip 18 of the coil into the soft tissue. Additional views are provided that show variations and embodiments that may allow for the coil 12 to fit into a specific location within the head of the screw.

Therefore, the coil can be utilized with a washer 11 in certain embodiments or without a washer 11, and instead through the use of the tunnel 37 or with the flanges on the base of the screw head. Each embodiment ensures that the coil 12 is rotated into the soft tissue when rotating the screw in a first direction, and then rotating the screw in the opposing direction to thread the screw into the bone.

The surgical screw 30 anchor preferably possesses properties to allow for the screw 30 to penetrate bone and anchor within the bone tissue. Accordingly, the screw 30 is preferably rigid to enable such penetration. Where the screw is maintained in the body, the screw is preferably stainless steel (316L) or titanium, or another metal or allow possessing similar flexural strength, pull-out strength, and stiffness. For example Magnesium based alloys Mg—Zn; Mg-6Nz; Mg—Zn—Ca; MGYREZr. Iron based alloys might include Fe—Mn.

However, in certain embodiments, the screw itself is bioresorbable and thus degrades in the body and is replaced by tissue ingrowth. However, to ensure that the mechanical properties of the screw are maintained for sufficient duration to enable healing of the injury, the mechanical properties should be maintained for at least 3 months, and preferably at least 6 months, before onset of degradation. Ultimately, complete degradation of an FDA approved biomaterial and replacement of said material with tissue ingrown is desired. Suitable materials include, but are not limited to certain polymers: PLLA, PLDLA (e.g. 70:30, 80:20 L/L); PLGA (e.g. 50:50 L/L); PLLA-PLGA block copolymers; poly (para-dioxanone) (PPD); poly (propylene fumarate) (PPF).

In certain embodiments, the screw may be manufactured of a composite having a coating polymer or metal bulk material or ceramic particular-reinforced polymer matrix. In certain instances, a coating/filler material might include CaP, Tricalcium phosphate; Hydroxyapatite (HA), and similar materials known for biocompatibility and use within the human body.

The coil material also has independent properties that assist in enabling the coil to effectively grip the soft tissue and to affix the soft tissue to adjacent bone tissue. In particular, the coil needs to possess shape memory, which limits its total deformation during deployment. This ensures that the coil is not simply deformed, but instead maintains sufficient rigidity and shape to grip into the soft tissue to enable the contact between tissue and bone for reattachment of the soft tissue.

The coil material may be manufactured of various polymers or metals, enabling both permanent and also bioresorbable production. The material preferably possesses physical properties similar to nitinol or platinum in flexural strength, pull-out strength, and stiffness.

Where the coil is bioresorbable, like the screw above, the material must have mechanical properties maintained for at least 3 months, and preferably for at least 6 months to enable healing of the injury before the onset of degradation. However, the material should completely degrade and be replaced by tissue ingrowth after a set amount of time. Suitable materials may include PLLA: PVA; PEG; PLA; poly (caprolactone)(PCL, ε-PCL); PLLA-PLGA; PEG-PCL; Chitosan (e.g. genipin-crosslinked); or other materials having similar profile for biocompatibility and bioresorbable. Where the material is maintained, metal alloys, composites and combinations thereof, including the same materials as the screw (detailed above) are suitable.

A washer 11 may optionally be utilized to assist with driving the coil and screw into the tissue (See e.g. FIG. 3A). The washer 11 may be unnecessary where the screw head is notched to guide coil placement as with the tunnel 37 and flange 36. The washer 11, may not be necessary to assist in tissue retention after initial placement. Accordingly, it may be made of a material that can quickly degrade after insertion. Accordingly, while the screw and coil require a duration of at least 3 months and preferably 6 months before they degrade, the washer 11 may begin degrading upon insertion. Like the above screw and coil, the washer can be made of the same or similar materials, including FDA-approved biomaterials or bioresorbable materials, such as those detailed above for the screw and coil, and including PGA, amorphous PLLA.

Figure 4:
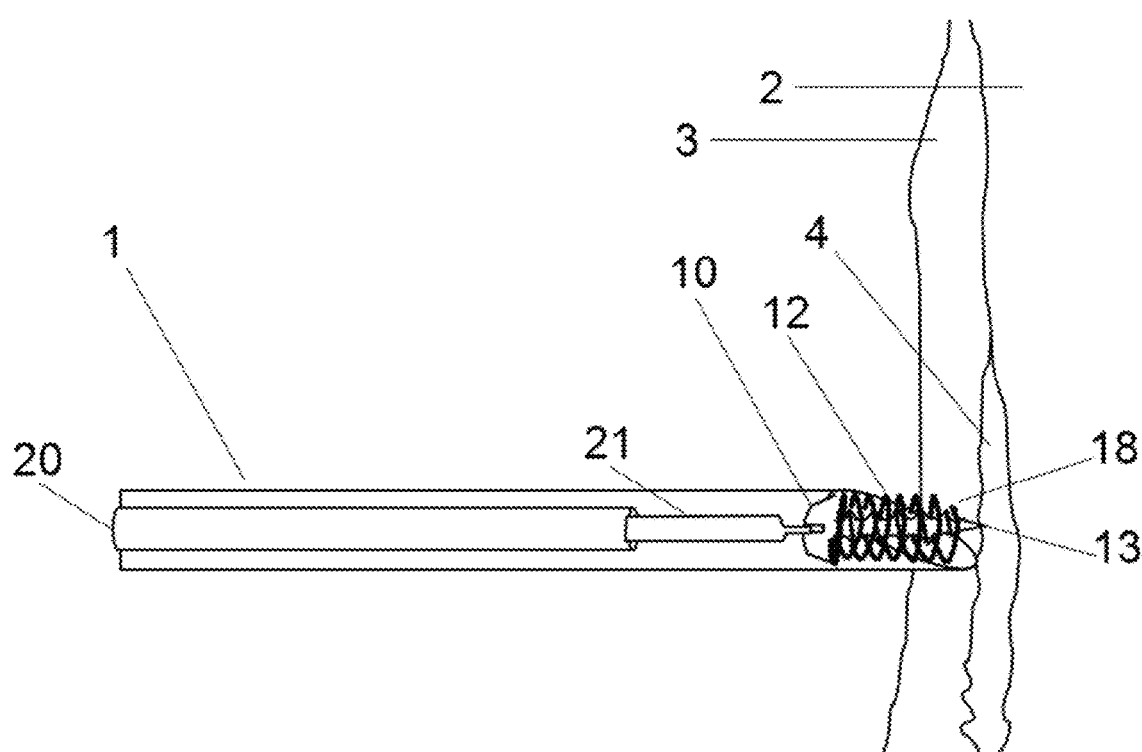
FIG. 4 depicts a screw being deployed through a needle into the soft tissue.

FIG. 4 depicts a sheath 20 for deploying a tool 21 to turn the screw 30. The screw 30 remains partially inside the needle aperture 5, with only a portion of the coil 12 and the shaft 13 projection out of the aperture 5. The tip of the shaft 13 is pressed into the soft tissue 3. The coil 12 is then released into the soft tissue 3.

Figure 5A:
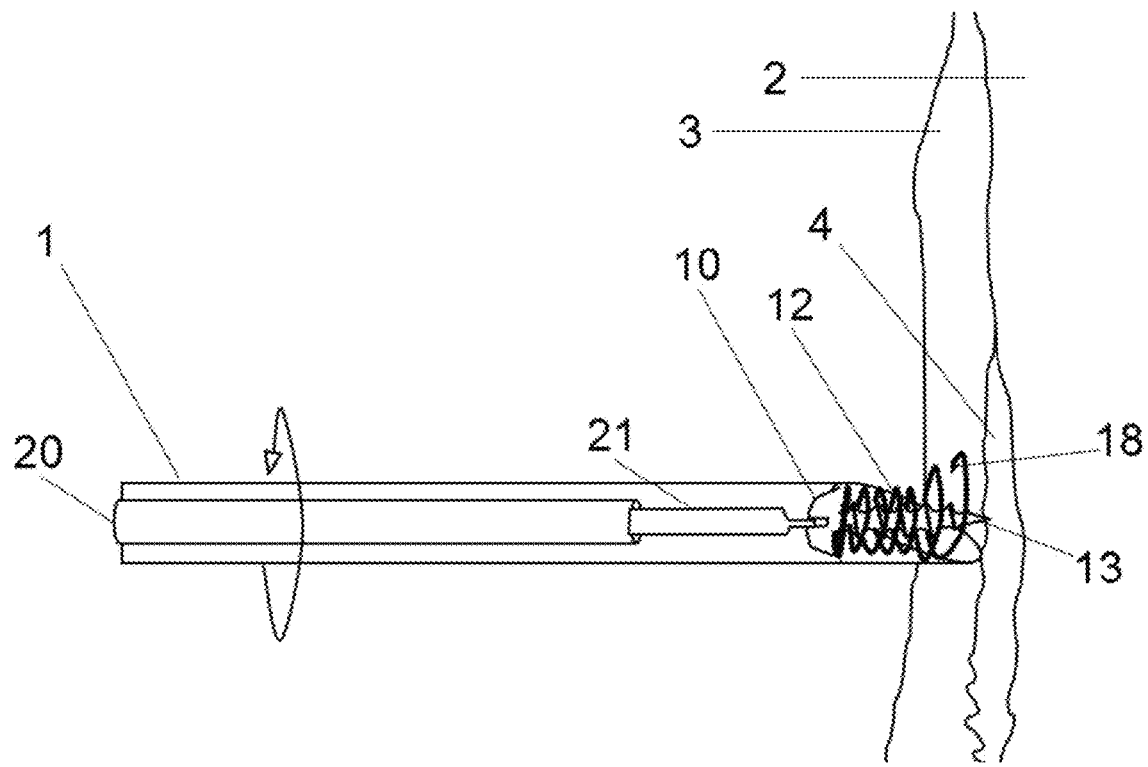
FIGS. 5A and 5B depicts a counter-clockwise turning of the screw, which deploys the coil into the soft tissue, with FIG. 5B depicting the rotation direction down the length of the tool.
Figure 5B:
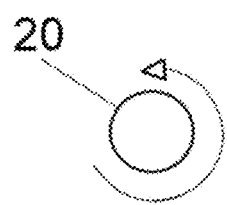

When the screw is turned in the counter-clockwise manner, the coil tip 18 engages into the soft tissue 3 and by rotating the screw 30 in the counter-clockwise manner, the coil 12, having several windings, functions like a screw, and rotates into the soft tissue 3 facilitated by the sharpened, outwardly curved tip 18. FIG. 5A depicts as the screw is rotated in the counter-clockwise manner (detailed by FIG. 5B), with the coil 12 deploying into the soft tissue 3.

Figure 6:
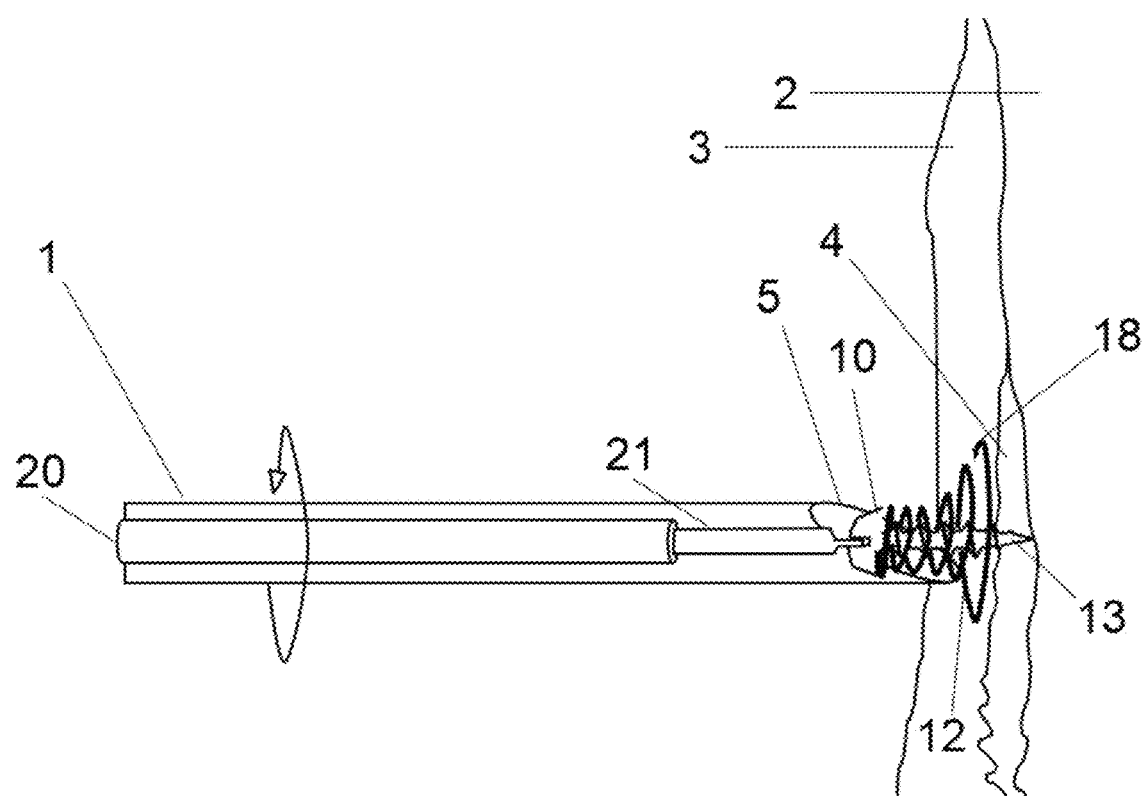
FIG. 6 depicts a further turned screw of FIG. 5.

FIG. 6 depicts the screw 30 with a further rotation in the counter-clockwise fashion to further deploy the coil 12 into the soft tissue 3. This can be visualized by the coil 12 having fewer windings tightly wrapped around the shaft 13 and the outer windings spread wider into the tissue, though there is no limitation for the device or methods described herein that requires the coil 12 to widely disseminate or deploy into the soft tissue 3.

Figure 7A:
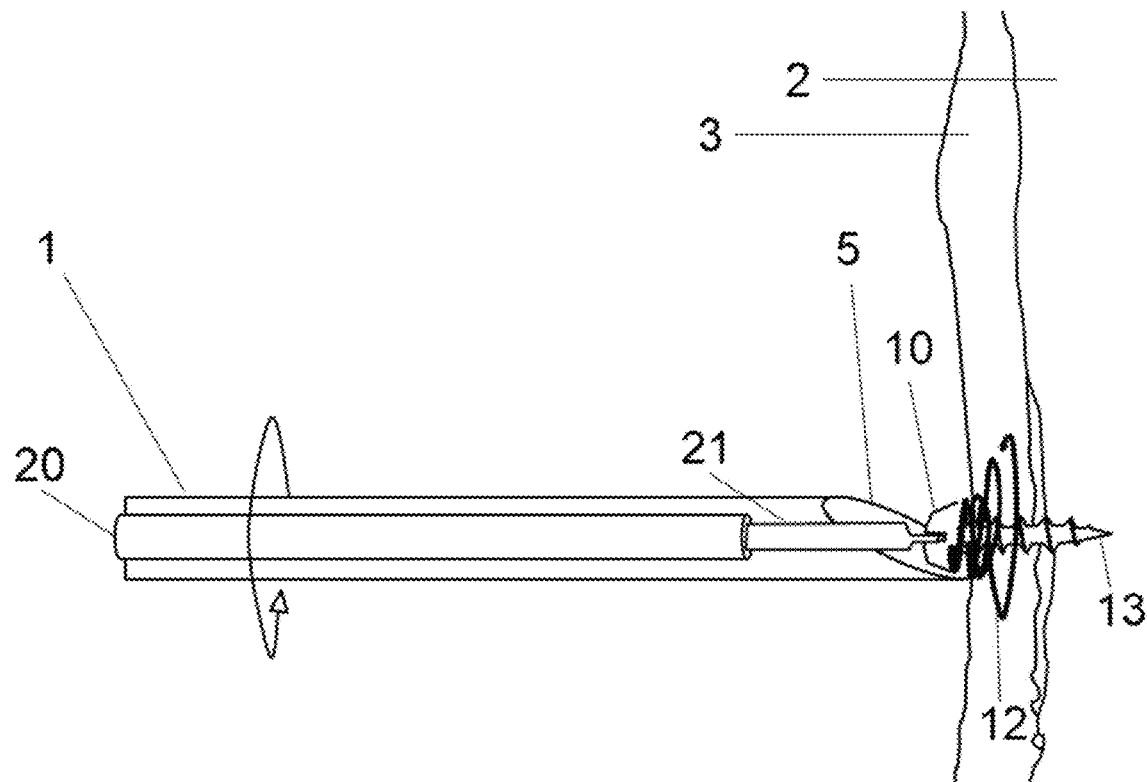
FIGS. 7A and 7B depict advancing the screw into the bone to secure the soft tissue to the bone, with FIG. 7B depicting the rotation direction down the length of the tool.
Figure 7B:
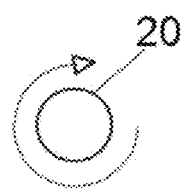

FIG. 7A depicts wherein the screw 30 is now advanced into the bone 2, with the shaft 13 now penetrating into the bone 2 by advancing the screw 30 in a clockwise manner (as detailed by FIG. 7B). By turning in a clockwise manner, the threads of the screw shaft 13 engage with the bone 2 and at the same time, there is no pressure on the coil head 15 from the lower offset limb 19, as the lower offset limb 19 will not contact the head flange 16, when rotated in the clockwise manner, the coil end 15 disengages from the offset limb 17, the coil held against the screw head 10 during advancement. As the screw 30 advances into the bone 2, the disengagement space 4 is reduced. A comparison between FIGS. 1 and 2 and FIG. 7A shows the disengagement space 4 is greatly reduced.

Figure 8:
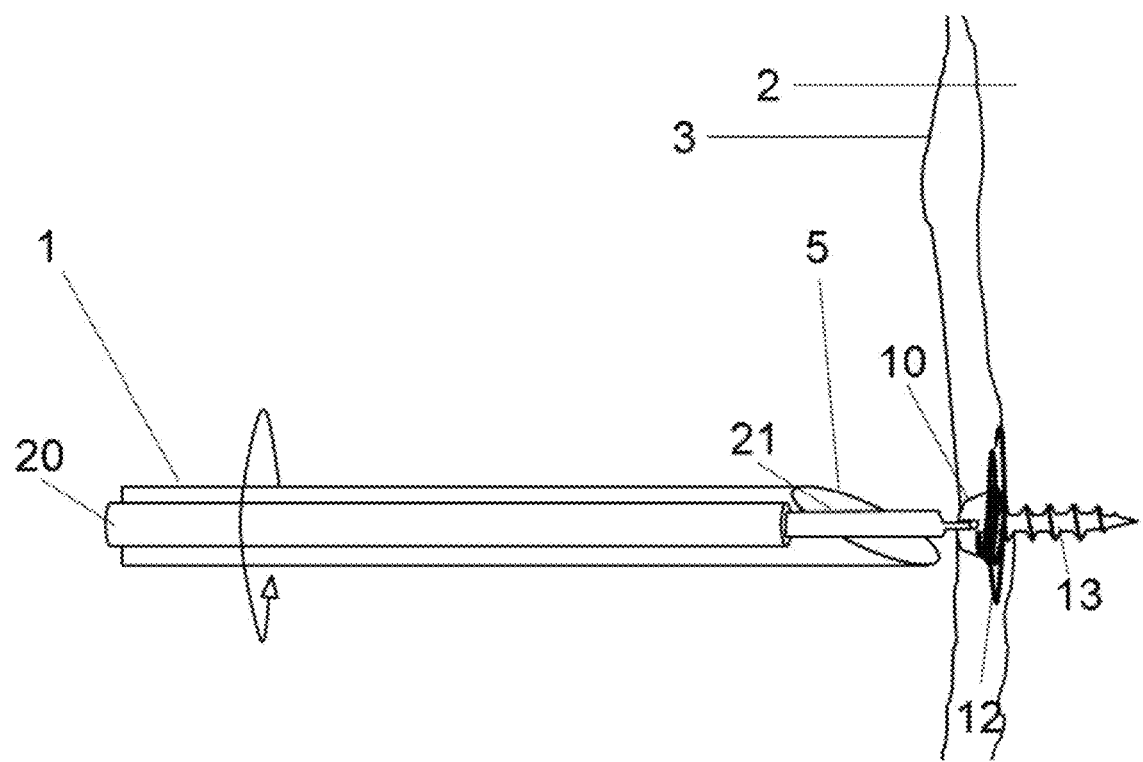
FIG. 8 depicts an advanced screw, with the coil deployed and the soft tissue compressed to the bone.

FIG. 8 depicts where the screw 30 is fully seated into the bone 2 and has compressed the soft tissue 3 against the bone 2. This allows the soft tissue 3 to heal and to re-attach to the bone 2 surface. It may be advantageous to add in certain compounds or therapeutics to the surgical site to enhance the healing process. Furthermore, it may be advantageous to coat the various components, the coil, and/or screw, or washer with certain therapeutics to enhance the healing process.

Figure 9:
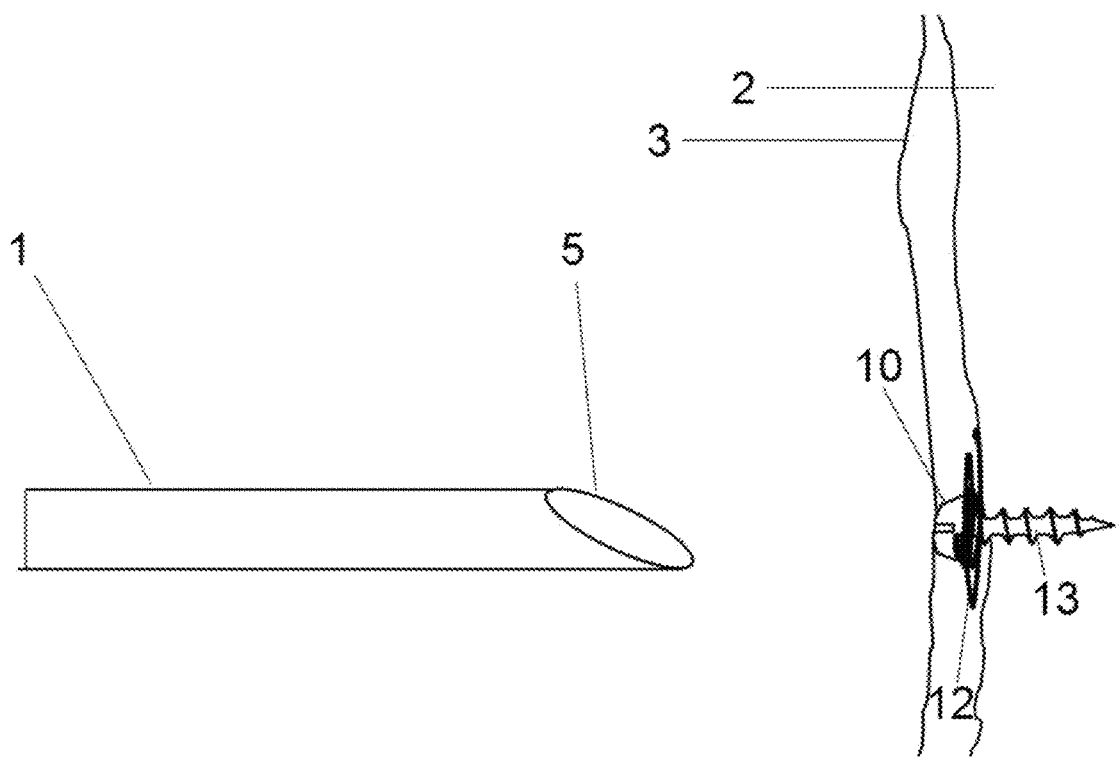
FIG. 9 depicts withdrawing the needle after the screw is implanted into the bone.

FIG. 9 shows the needle 1 withdrawing from the surgical site, with the screw implanted into the bone 2 with the coil 12 deployed into the soft tissue 3.

Accordingly, the device functions by provided a screw, having threads in a first direction and a coil 12 wound around the threads wound in the opposing direction. Rotation of the screw in the direction of the wound coil, will wind the coil into the soft tissue. This requires that the coil is of sufficient rigidity so as to enable the coil tip 18 to penetrate the soft tissue 3. Furthermore, continued rotation of the screw in the direction of the wound coil, requires that the coil, once in the soft tissue 3, is sufficiently rigid to continue to be driven into the soft tissue 3. As the coil 12 rotates, the coil 12 deploys into the soft tissue 3 and is embedded into the soft tissue 3. This ensures that the coil 12 is holding the soft tissue 3 in an area that is wider than the head 30 of the screw, and through a variety of tissues.

Then, the screw shaft 13 can be driven through the soft tissue 3 and into the bone 2. The screw is rotated in the direction of the threads, so that the screw shaft 13 is embedded into the bone. By fastening the screw head against the soft tissue 3, the soft tissue 3 is compressed against the bone 2. The contact between the two tissues allows healing process to occur, where the soft tissue 3 is normally attached to the bone 2.

Certain bone or vascular stimulators can be utilized to stimulate healing at the surgical site. Indeed, these can be coated onto the screw and or coil, or combinations thereof, or injected to, or applied to the surgical area through the needle during the surgical procedure.

A preferred embodiment comprises a method of repairing a soft tissue when disassociated from a bone comprising; inserting a surgical tool, comprising an aperture for inserting a screw and a tool to turn the screw; said screw comprising a shaft having threads in a first direction, a washer, having offset limbs, a head having a bottom face having a flange, and a coil; said coil wound around the screw shaft in an opposing second direction as to the first direction; said coil comprising a coil end which is defined to engage with an offset limb of said washer; a second offset limb of said washer engages to the flange on the bottom face; engaging the end of the shaft and the coil to a soft tissue; rotating the screw in the second direction until said coil is deployed into said tissue a pre-determined amount; rotating said screw in a first direction, until said screw is sufficiently embedded into a bone surface to compress said soft tissue to said bone.

Alternatively, an embodiment comprises a screw having a tunnel and no washer in the component and this describes a method of repairing a soft tissue when disassociated from a bone comprising; inserting a surgical tool, comprising an aperture for inserting a screw and a tool to turn the screw; said screw comprising a shaft having threads in a first direction, a head having a bottom face having a flange with a tunnel, and a coil; said coil wound around the screw shaft in an opposing second direction as to the first direction; said coil comprising a coil end which is defined to engage with said flange tunnel; engaging the end of the shaft and the coil to a soft tissue; rotating the screw in the second direction until said coil is deployed into said tissue a pre-determined amount; rotating said screw in a first direction, until said screw is sufficiently embedded into a bone surface to compress said soft tissue to said bone.

Further embodiments and methods of the above can utilize an embodiment having no washer and no tunnel, wherein a flange on the bottom face of the screw head engages with the coil. Such device can be exchanged in either method above.

Further embodiments describe use of a dual-function anchor system to engage a displaced soft tissue, engage said soft tissue with a coil, and drive the soft tissue, having the embedded coil, to contact a bone, by driving a screw into the bone. Said dual-function anchor system comprises a surgical screw comprising a shaft having threads in a first direction, a head having a bottom face having a flange, and a coil; said coil wound around the screw shaft in an opposing second direction as to the first direction; said coil comprising a coil end which is defined to engage said flange; engaging the end of the shaft and the coil to a soft tissue. Further embodiments may comprise a washer, a flange tunnel, and/or indentations to aid in pressing the coil in a first direction and releasing the coil upon turning the screw in a second, opposing direction.

In certain preferred embodiments, and methods of treatment, it may be suitable to drive the dual-function anchor system comprising a screw and a coil into the tissue of a patient. Before or after engaging the tissues, the aperture for the dual-function anchor system may further be utilized to inject certain bone or vascular healing compositions to the surgical site.

Accordingly, methods of treatment may comprise the above methods, further comprising a step of injecting a therapeutic to the wound site, for example a bone or vascular healing composition. A further therapeutic may include antibiotics. In certain embodiments, the coil or the screw may be coated with a therapeutic, including a bone or vascular healing composition or an antibiotic. Those of ordinary skill in the art will recognize these compounds and their appropriate doses for administration. For example a non-limiting list of antibiotics may include clindamycin, trimethoprim/sulfamethoxazole, doxycycline, vancomycin, linezolid, daptomycin, metronidazole or combinations thereof.

What is claimed is:

1. A surgical screw comprising:
    a self-tapping orthopedic screw shaft having threads in a first direction; and
    a screw head defining a tunnel; and
    a coil wound around the self-tapping orthopedic screw shaft in an opposing second direction relative to the first direction, the coil comprising:
        a first coil end adapted and configured to engage with the tunnel of the screw head; and
        a second coil end adapted and configured to engage soft tissue when the surgical screw is rotated in the second direction.

2. The surgical screw of claim 1, wherein the tunnel and the first coil end are adapted and configured to release the first coil end when the surgical screw is rotated in the first direction.

3. The surgical screw of claim 1, wherein one or more of the self-tapping orthopedic screw shaft, the screw head, and the coil are made of bio-compatible materials.

4. The surgical screw of claim 1, wherein one or more of the self-tapping orthopedic screw shaft, the screw head, and the coil are coated with a bone or vascular stimulator.

5. The surgical screw of claim 1, wherein one or more of the self-tapping orthopedic screw shaft, the screw head, and the coil are bio-absorbable.

6. The surgical screw of claim 1, wherein one or more of the self-tapping orthopedic screw shaft, the screw head, and the coil comprise one or more materials selected from the group consisting of: poly(L-lactic acid), poly(D-L-lactic acid), poly(lactic-co-glycolic acid), poly(para-dioxanone), poly(propylene fumarate), copolymers of poly(L-lactic acid and poly(lactic-co-glycolic acid), magnesium-based alloys, Mg—Zn alloys, Mg—6Zn alloys, Mg—Zn—Ca alloys, MgYREZr alloys, iron-based alloys, and Fe—Mn alloys.

7. The surgical screw of claim 1, wherein one or more of the self-tapping orthopedic screw shaft, the screw head, and the coil comprise a polymer coating on a metal.

8. The surgical screw of claim 1, wherein one or more of the self-tapping orthopedic screw shaft, the screw head, and the coil comprise a ceramic material selected from the group consisting of: calcium phosphate, tricalcium phosphate, and hydroxyapatite in a particulate-reinforced polymer matrix.

9. The surgical screw of claim 1, wherein one or more of the self-tapping orthopedic screw shaft, the screw head, and the coil comprise a ceramic material selected from the group consisting of: calcium phosphate, tricalcium phosphate, and hydroxyapatite as a coating.

10. The surgical screw of claim 1, wherein one or more of the self-tapping orthopedic screw shaft, the screw head, and the coil comprise one or more selected from the group consisting of: amorphous poly(lactic acid), poly(L-lactic acid), poly(D-L-lactic acid), poly(lactic-co-glycolic acid), poly(ethylene glycol), poly(caprolactone), copolymers of poly(L-lactic acid and poly(lactic-co-glycolic acid), copolymers of poly(ethylene glycol) and poly(caprolactone), chitosan crosslinked with or without genipin, magnesium-based alloys, Mg—Zn alloys, Mg—6Zn alloys, Mg—Zn—Ca alloys, MgYREZr alloys, iron-based alloys, and Fe—Mn alloys.

11. The surgical screw of claim 1, wherein one or more of the self-tapping orthopedic screw shaft, the screw head, and the coil are non-absorbable.

12. A surgical tool comprising:
    the surgical screw of claim 1;
    a needle having an aperture of sufficient diameter for receiving the surgical screw; and
    a tool adapted and configure for insertion within the aperture and rotational engagement of the surgical screw.

13. The surgical tool of claim 12, wherein the needle has a beveled distal end.

14. A method of repairing a soft tissue when disassociated from a bone, the method comprising:
    inserting the surgical tool of claim 12 into the soft tissue;
    engaging the end of the self-tapping orthopedic screw shaft and the second coil to the soft tissue;
    rotating the surgical screw in the second direction until the coil is deployed into the soft tissue a pre-determined amount; and
    rotating the surgical screw in the first direction until the surgical screw is sufficiently embedded into the bone to compress the soft tissue to the bone.

15. A method of repairing a soft tissue when disassociated from a bone, the method comprising:
    inserting the surgical screw of claim 1 into the soft tissue;
    engaging the end of the self-tapping orthopedic screw shaft and the second coil to the soft tissue;
    rotating the surgical screw in the second direction until the coil is deployed into the soft tissue a pre-determined amount; and
    rotating the surgical screw in the first direction until the surgical screw is sufficiently embedded into the bone to compress the soft tissue to the bone.

16. The surgical screw of claim 1, wherein the tunnel is substantially tangential to the screw head.

17. A surgical screw comprising a self-tapping orthopedic screw shaft having threads in a first direction, a head having a bottom face having a flange, and a coil; said coil wound around the self-tapping orthopedic screw shaft in an opposing second direction as to the first direction; said coil comprising a coil end which is defined to engage said flange; engaging the end of the self-tapping orthopedic screw shaft and the coil to a soft tissue.

18. The surgical screw of claim 17 comprising wherein said flange has a tunnel and wherein the coil end engages into the tunnel.

19. The surgical screw of claim 17, said coil comprising an outward curved tip having a beveled face open at inner aspect.

* * * * *